(12) United States Patent
Bommakanti et al.

(10) Patent No.: US 11,667,758 B2
(45) Date of Patent: Jun. 6, 2023

(54) TEMPERATURE-INSENSITIVE MEMBRANE MATERIALS AND ANALYTE SENSORS CONTAINING THE SAME

(71) Applicant: Abbott Diabetes Care Inc., Alameda, CA (US)

(72) Inventors: Balasubrahmanya S. Bommakanti, Alameda, CA (US); John V. Latour, Alameda, CA (US); Udo Hoss, Alameda, CA (US); Tianmei Ouyang, Alameda, CA (US); Phu Le, Alameda, CA (US); Gary Sandhu, Alameda, CA (US); Kevin Wallis, Alameda, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 938 days.

(21) Appl. No.: 16/474,790

(22) PCT Filed: Jun. 11, 2019

(86) PCT No.: PCT/US2019/036469
§ 371 (c)(1),
(2) Date: Jun. 28, 2019

(87) PCT Pub. No.: WO2019/241192
PCT Pub. Date: Dec. 19, 2019

(65) Prior Publication Data
US 2022/0002498 A1    Jan. 6, 2022

Related U.S. Application Data

(60) Provisional application No. 62/684,438, filed on Jun. 13, 2018.

(51) Int. Cl.
| | |
|---|---|
| C08G 81/02 | (2006.01) |
| C08G 65/333 | (2006.01) |
| C08J 5/18 | (2006.01) |
| A61B 5/145 | (2006.01) |
| A61B 5/1486 | (2006.01) |
| A61B 5/1495 | (2006.01) |

(52) U.S. Cl.
CPC ........ *C08G 81/025* (2013.01); *A61B 5/14532* (2013.01); *A61B 5/14865* (2013.01); *C08G 65/33317* (2013.01); *C08J 5/18* (2013.01); *A61B 5/1495* (2013.01); *C08J 2339/08* (2013.01)

(58) Field of Classification Search
CPC ..... C08L 39/04; C08J 2339/08; C08F 226/06; C08G 81/025
See application file for complete search history.

(56) References Cited

U.S. PATENT DOCUMENTS

| | | | |
|---|---|---|---|
| 9,775,544 B2 | 10/2017 | Ouyang et al. | |
| 9,775,549 B2 | 10/2017 | Ouyang et al. | |
| 2014/0026646 A1* | 1/2014 | Feldman | G01N 27/327 73/61.43 |
| 2015/0001074 A1 | 1/2015 | Liu | |
| 2016/0045147 A1* | 2/2016 | Ouyang | A61B 5/14532 600/309 |

FOREIGN PATENT DOCUMENTS

| | | |
|---|---|---|
| JP | 2000-514791 A | 11/2000 |
| JP | 2005-520172 A | 7/2005 |
| WO | WO 97/49736 A2 | 12/1997 |
| WO | WO 03/085372 A2 | 10/2003 |

OTHER PUBLICATIONS

ISR-WO dated XX for related matter PCT/US2019/036469 (The ISR also cited to US 2016045147, and applicant notes that the issued patent related to that publication was already submitted in an IDS).

* cited by examiner

*Primary Examiner* — Jeffrey C Mullis
(74) *Attorney, Agent, or Firm* — Sterne, Kessler, Goldstein & Fox P.L.L.C.

(57) ABSTRACT

Membranes permeable to an analyte may overlay the active sensing region of a sensor to limit the analyte flux and improve the response linearity of the sensor. Temperature variation of the analyte permeability can be problematic in some instances. Polymeric membrane compositions having limited variation in analyte permeability as a function of temperature may comprise: a polymer backbone comprising one or more side chains that comprise a heterocycle; and an amine-free polyether arm appended, via an alkyl spacer or a hydroxy-functionalized alkyl spacer, to the heterocycle of at least a portion of the one or more side chains.

26 Claims, 5 Drawing Sheets

TEMPERATURE-INSENSITIVE MEMBRANE MATERIALS AND ANALYTE SENSORS CONTAINING THE SAME

BACKGROUND

The detection of various analytes within an individual can sometimes be vital for monitoring the condition of their health. Deviation from normal analyte levels can often be indicative of a number of physiological conditions. Glucose levels, for example, can be particularly important to detect and monitor in diabetic individuals. By monitoring glucose levels with sufficient regularity, a diabetic individual may be able to take corrective action (e.g., by injecting insulin to lower glucose levels or by eating to raise glucose levels) before significant physiological harm occurs. Other analytes commonly subject to physiological dysregulation that may similarly be desirable to monitor include, but are not limited to, lactate, oxygen, pH, A1c, ketones, drug levels, and the like.

Analyte monitoring in an individual may take place periodically or continuously over a period of time. Periodic analyte monitoring may take place by withdrawing a sample of bodily fluid, such as blood, at set time intervals and analyzing ex vivo. Continuous analyte monitoring may be conducted using one or more sensors that remain at least partially implanted within a tissue of an individual, such as dermally, subcutaneously or intravenously, so that analyses may be conducted in vivo. Implanted sensors may collect analyte data continuously or sporadically, depending on an individual's particular health needs and/or previously measured analyte levels.

Periodic, ex vivo analyte monitoring can be sufficient to determine the physiological condition of many individuals. However, ex vivo analyte monitoring may be inconvenient or painful for some persons. Moreover, there is no way to recover lost data if an analyte measurement is not obtained at an appropriate time.

Continuous analyte monitoring with an in vivo implanted sensor may be a more desirable approach for individuals having severe analyte dysregulation and/or rapidly fluctuating analyte levels, although it can also be beneficial for other individuals as well. While continuous analyte monitoring with an implanted sensor can be advantageous, there are challenges associated with these types of measurements. Intravenous analyte sensors have the advantage of providing analyte concentrations directly from blood, but they are invasive and can sometimes be painful for an individual to wear over an extended period. Subcutaneous and dermal analyte sensors can often be less painful for an individual to wear and can provide sufficient measurement accuracy in many cases.

Although the entirety of a sensor may be implanted within an individual (e.g., surgically), it is often more desirable for primarily the active portion of the sensor to be implanted internally (e.g., through a skin penetration), with one or more additional sensor components remaining external to the individual's body. In certain instances, sensors suitable for measuring analyte levels in vivo may extend from a sensor housing that is designed to be worn "on-body" for extended periods of time, such as upon the skin. Such on-body analyte sensors may be especially desirable, since they often may be applied directly by a wearer, rather than relying on a medical professional to perform an invasive sensor implantation procedure.

Sensors may include a membrane disposed over at least the implanted portion of the sensor. In one aspect, the membrane may improve biocompatibility of the sensor in vivo. In another aspect, the membrane may be permeable or semi-permeable to an analyte of interest but limit the overall flux of the analyte to the active sensing portion of the sensor. Limiting access of the analyte to the active sensing portion of the sensor can aid in avoiding overloading (saturating) the active sensing components, thereby improving sensor performance and accuracy. For example, in the case of sensors employing enzyme-based detection, limiting access of the analyte to the sensor can make the chemical kinetics of the sensing process analyte-limited rather than enzyme-limited. With the enzymatic reaction being analyte-limited, ready calibration of the analyte sensor as a function of the sensor output may be realized. That is, the sensor output may be correlated in some manner to the amount of analyte when the enzymatic reaction is analyte-limited. In many instances, the sensor response may vary linearly as a function of the analyte concentration in a biological fluid of interest when the enzymatic reaction is analyte-limited.

One issue associated with incorporating a membrane upon an analyte sensor is that the analyte flux across the membrane may vary considerably as a function of temperature. While a calibration factor or equation may be employed to account for analyte flux variability as a function of temperature, doing so can add considerable complexity to use of the sensor, especially if the analyte flux is non-linear with respect to temperature. Moreover, thermistors used in applying a calibration equation may be complicated to operate and their size may thwart sensor miniaturization efforts. As another difficulty, the calibration temperature measurement location may not necessarily have the same temperature as the membrane covering an active portion of the sensor. Other components of the sensor may likewise exhibit performance variability with temperature (e.g., the enzymatic reaction rate in the case of an enzyme-based sensor), which can make isolation and application of a calibration factor or equation for the membrane rather difficult. With increasing component complexity and performance variability, higher costs and growing measurement errors may result.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

DETAILED DESCRIPTION

Figure 1:
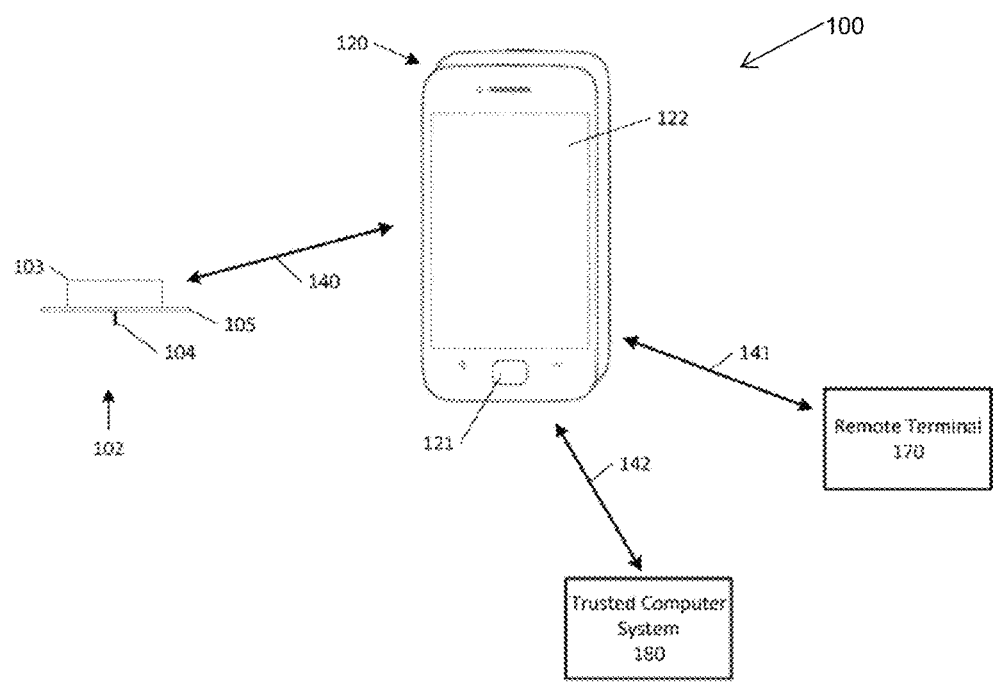
FIG. 1 shows a diagram of an illustrative analyte monitoring system that may incorporate an analyte sensor of the present disclosure.

The present disclosure generally describes analyte sensors suitable for in vivo use and, more specifically, membrane materials that exhibit limited analyte permeability variation as a function of temperature and analyte sensors incorporating such membrane materials.

As discussed above, in vivo analyte sensors may incorporate a membrane material in order to improve biocompatibility and to limit access of an analyte to the active sensing region of the sensor. Limiting analyte access to the sensing region can aid in avoiding sensor saturation, thereby improving sensor performance and accuracy. In the case of an enzymatic sensor, for example, a membrane material can promote an analyte-limited detection process rather than an enzyme-limited detection process. With the detection process being analyte-limited, ready sensor calibration may be realized. In some instances, the sensor response may vary linearly as a function of analyte concentration in an analyte-limited detection process.

One difficulty associated with many membrane materials is that their analyte permeability may vary to a clinically significant degree as a function of temperature. Analyte permeability variation as a function of temperature can lead to problematic sensor calibration, especially if the permeability variation is non-linear with respect to temperature. While certain membrane materials are known to exhibit limited analyte permeability variation as a function of temperature, their biocompatibility properties may leave room for improvement. Further, some membrane materials may be difficult to purify following synthesis.

The present disclosure provides polymeric membrane compositions that, in certain embodiments, may provide a desirable combination of limited analyte permeability variation as a function of temperature and favorable biocompatibility properties. More specifically, the polymeric membrane compositions disclosed herein include a polymer backbone having one or more side chains that comprise a heterocycle (also referred to herein as a heterocyclic polymer), and an amine-free polyether arm appended to at least a portion of the one or more side chains, particularly to at least a portion of the heterocycles. The amine-free polyether arm may incorporate one or more polyethylene glycol portions (blocks) and one or more polypropylene glycol portions (blocks), which may be appended to the heterocycle via an alkyl spacer or a hydroxy-functionalized alkyl spacer. Other spacers such as carbonyls, carboxylic esters, or carboxamides, for example, may also be suitable in some embodiments. In some embodiments, a single polyethylene glycol portion may be bonded to a single polypropylene glycol portion in a diblock arrangement (e.g., in a A-B block pattern or a B-A block pattern, where A is a polyethylene glycol block and B is a polypropylene glycol block) in the amine-free polyether arms. In other more particular embodiments, the one or more polyethylene glycol portions and the one or more polypropylene glycol portions may be present in alternating blocks, without intervening functionality being present (e.g., in an A-B-A pattern, according to some embodiments, or in a B-A-B pattern, according to other embodiments, where A is a polyethylene glycol block and B is a polypropylene glycol block). The amine-free polyether arms may likewise comprise more than three alternating blocks, according to further embodiments of the present disclosure. Both the block pattern and number of ether units in each block may be varied in the polymeric membrane compositions disclosed herein. In some embodiments, a terminal polyethylene glycol unit within the amine-free polyether arm may be appended to the heterocycle or other side chain in the heterocyclic polymer via the alkyl spacer or the hydroxy-functionalized alkyl spacer, or alternative spacers such as carbonyls, carboxylic esters, or carboxamides. In other embodiments, a terminal polypropylene glycol unit within the amine-free polyether arm may be appended to the heterocycle or other side chain in the heterocyclic polymer via the alkyl spacer or the hydroxyl-functionalized alkyl spacer, or alternative spacers such as carbonyls, carboxylic esters, or carboxamides.

The polymeric membrane compositions of the present disclosure may be synthesized by reacting a heterocyclic polymer with a polyether arm precursor bearing a reactive functionality, such as a terminal leaving group, particularly an alkyl halide or a terminal epoxide. More specifically, a primary alkyl halide, such as a primary alkyl bromide, may terminate an amine-free polyether arm precursor and lead to an alkyl spacer appending the amine-free polyether arm to a heterocycle. Epoxide termination of the amine-free polyether arm precursor, in contrast, results in the amine-free polyether arm becoming appended to a heterocycle via a hydroxy-functionalized alkyl group, specifically an alkyl group bearing a secondary hydroxyl functionality. Selection of a particular amine-free polyether arm precursor, including the choice of reactive functionality, may be based upon factors such as synthetic ease, in vivo properties of the resulting polymer, and the like. In more particular configurations, a primary alkyl halide or an epoxide may be bonded to a polyethylene glycol portion of the amine-free polyether arm precursor (i.e., through a terminal ether linkage and intervening spacer group). In other particular configurations, a primary alkyl halide or an epoxide may be bonded to a polypropylene glycol portion of the amine-free polyether arm precursor (i.e., through a terminal ether linkage and intervening spacer group).

Advantageously, the amine-free polyether arm precursors described herein may be synthesized independently before being reacted with a heterocyclic polymer. Independent synthesis of the amine-free polyether arm precursors may provide greater compositional homogeneity of the side chains in the resulting polymeric membrane compositions, as compared to that obtainable by stepwise growth of the arms from a polymer backbone, in which differing arm lengths may be produced. Moreover, by reacting an amine-free polyether arm precursor in one step with a polymer backbone, improved yields, greater synthetic convergency, and higher throughput may be realized, which may allow changes in membrane properties to be more readily correlated with structural variation. A further advantage of the polymeric membrane compositions disclosed herein is that they may, in many instances, be synthesized with a higher degree of purity and compositional homogeneity than are comparable polymer compositions bearing an amine functionality within the polyether arms.

A further advantage of the present disclosure is that the ratio of polyethylene oxide to polypropylene oxide within the presently disclosed polymeric membrane compositions may be varied much more readily than in similar polymer compositions bearing an amine functionality within the polyether arms. More specifically, the distribution and ratio of polyethylene oxide to polypropylene oxide may be fixed within an amine-free polyether arm precursor before bonding to the heterocyclic polymer takes place. Advantageously and surprisingly, this feature may allow tailoring of the ratio of polyethylene glycol to polypropylene glycol to promote a desired biological response in vivo, as discussed further herein.

At least some of the polymeric membrane compositions disclosed herein may exhibit low or non-existent cytotoxicity in vivo, as well as other favorable biocompatibility properties. In particular embodiments, the ratio of polyethylene oxide to polypropylene oxide may tailor the biocompatibility properties obtained, such that the polymeric membrane compositions may be characterized as having a cytotoxicity score of 2 or below, as measured by the Minimal Essential Elution Media Test. In some or other particular embodiments, the polymeric membrane compositions described herein meet the biocompatibility requirements specified in International Standards Organization (ISO) 10993-1 when evaluated according to the test protocols specified therein.

As such, the polymeric membrane compositions disclosed herein can be particularly advantageous for use in various in vivo analyte sensors, particularly when the analyte sensors are intended for extended wear. It is to be appreciated, however, that the polymeric membrane compositions disclosed herein may also be utilized in ex vivo analyte sensors without departing from the scope of the present disclosure. In particular embodiments, the polymeric membrane compositions described herein may be temperature-insensitive toward permeability of glucose. Other analytes such as lactate, for example, may also permeate through the polymeric membrane compositions at temperature-insensitive rates, which may differ from that of glucose.

Accordingly, in some embodiments, polymeric membrane compositions of the present disclosure may comprise a polymer backbone comprising one or more side chains that comprise a heterocycle, and an amine-free polyether arm appended, via an alkyl spacer or a hydroxy-functionalized alkyl spacer, to the heterocycle of at least a portion of the one or more side chains. Such amine-free polyether arms are distinguished from crosslinkers (i.e., a group covalently joining two or more polymer backbones together) by virtue of the characteristic that the amine-free polyether arms are bonded to a single polymer backbone.

Polymers suitable for use in the various embodiments of the present disclosure may comprise a polymer backbone that is branched or unbranched and that is a homopolymer or a heteropolymer. Homopolymers may be formed by polymerization of a single type of monomer. Heteropolymers (also referred to as copolymers) include two or more different types of monomers bonded in a single polymer chain. Copolymers can have a random, alternating, or block distribution of the differing monomer units, according to various embodiments.

Heterocycles suitable for incorporation within the polymeric membrane compositions of the present disclosure may comprise any cyclic moiety containing one or more carbon atoms in conjunction with any combination of N, P, O, S or Si atoms, in which the cyclic moiety may be aromatic or aliphatic. Suitable functional groups incorporating a heteroatom within an aliphatic or heteroaromatic cyclic moiety may include, for example, —O—, —S—, —S—S—, —O—S—, —NR$^1$R$^2$, =N—, =N—N=, —N=N—, —N=N—NR$^1$R$^2$, —PR$^3$—, —P(O)$_2$—, —P(O)R$^3$—, —O—P(O)$_2$—, —S—O—, —S(O)—, —S(O)$_2$—, and the like, wherein R$^1$-R$^3$ are independently hydrogen, alkyl, substituted alkyl, alkenyl, substituted alkenyl, alkynyl, substituted alkynyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl. Where feasible, any of R$^1$-R$^3$ may be linear or branched. Substituted variants of R$^1$-R$^3$ may include any of the aforementioned groups in which a carbon atom or a hydrogen atom has been replaced by a heteroatom such as F, Cl, Br, I, N, P, O, S or Si. In illustrative but non-limiting embodiments, suitable substitutions may include, for example, halide groups, alcohol groups, ketone groups, ether groups, thioether groups, disulfide groups, and the like.

In more specific embodiments, the polymer backbone may comprise a heterocyclic or heteroaromatic nitrogen moiety within the one or more side chains. In still more specific embodiments, the polymer backbone may comprise a heteroaromatic nitrogen moiety within the one or more side chains. Suitable heteroaromatic nitrogen moieties may include, for example, acridine, carbazole, carboline, cinnoline, imidazole, indazole, indole, indoline, indolizine, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyrazine, pyrazole, pyridazine, pyridine, pyrimidine, pyrrole, pyrrolizine, quinazoline, quinoline, quinolizine, quinoxaline, tetrazole, thiadiazole, thiazole, triazole, derivatives thereof, and the like.

One or more co-monomers may be present in combination with a monomer unit bearing a heteroaromatic nitrogen moiety, according to some embodiments. Suitable co-monomers for incorporation in the polymeric membrane compositions of the present disclosure include, for example, styrene compounds, optionally bearing substitution on the aromatic ring. Substituted styrene compounds that may be suitable include, for example, alkyl-substituted styrenes, halogen-substituted styrenes, hydroxyl-substituted styrenes, or any combination thereof.

In more specific embodiments, polymeric membrane compositions of the present disclosure may comprise a polyvinylpyridine or a polyvinylimidazole, including any copolymer thereof. In particular embodiments, the polymeric membrane compositions of the present disclosure may comprise a polyvinylpyridine, particularly a copolymer of vinylpyridine (particularly 4-vinylpyridine) and styrene, or a polyvinylimidazole, particularly a copolymer of vinylimidazole (particularly 2-vinylimidazole) and styrene. Substituted styrenes may be utilized in some embodiments.

According to certain embodiments, a suitable copolymer of 4-vinylpyridine and styrene may comprise the repeating unit of Formula 1, in which variables a and b are both positive integers, and Q is optional functionality.

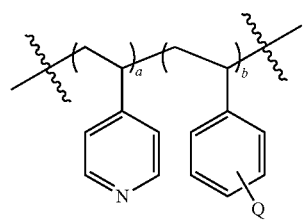

Formula 1

In some embodiments, variables a and b may independently range from about 1 to about 1000, including ranges of about 2 to about 950, or about 5 to about 900, or about 10 to about 850, or about 15 to about 800, or about 20 to about 750, or about 25 to about 700, or about 30 to about 650, or about 35 to about 600, or about 40 to about 550, or about 50 to about 500, or 1 to about 10. In some embodiments, a may be greater than b. In other embodiments, a may be less than b. Depending on the membrane properties desired, a ratio of a to b may range from about 1:1 to about 1:100, or from about 1:1 to about 1:95, or from 1:1 to about 1:80, or from 1:1 to about 1:75, or from about 1:1 to about 1:50, or from about 1:1 to about 1:25, or from about 1:1 to about 1:10, or from about 1:1 to about 1:5, or from about 1:1 to about 1:3, or from about 1:1 to about 1:2, or from about 1:1 to about 100:1, or from about 1:1 to about 95:1, or from about 1:1 to about 80:1, or from about 1:1 to about 75:1, or from about 1:1 to about 50:1, or from about 1:1 to about 25:1, or from about 1:1 to about 10:1, or from about 1:1 to about 5:1, or from about 1:1 to about 3:1, or from about 1:1 to about 2:1.

In some or other embodiments, a suitable copolymer of 4-vinylpyridine and styrene may have a styrene content ranging from about 0.01% to about 50% mole percent, or from about 0.05% to about 45% mole percent, or from about 0.1% to about 40% mole percent, or from about 0.5% to about 35% mole percent, or from about 1% to about 30% mole percent, or from about 2% to about 25% mole percent, or from about 5% to about 20% mole percent. Substituted styrenes may be used similarly and in similar amounts.

According to some or other various embodiments, a suitable copolymer of 4-vinylpyridine and styrene may have a molecular weight of 5 kDa or more, or about 10 kDa or more, or about 15 kDa or more, or about 20 kDa or more, or about 25 kDa or more, or about 30 kDa or more, or about 40 kDa or more, or about 50 kDa or more, or about 75 kDa or more, or about 90 kDa or more, or about 100 kDa or more. In more specific embodiments, a suitable copolymer of 4-vinylpyridine and styrene may have a molecular weight ranging from about 5 kDa to about 150 kDa, or from about 10 kDa to about 125 kDa, or from about 15 kDa to about 100 kDa, or from about 20 kDa to about 80 kDa, or from about 25 kDa to about 75 kDa, or from about 30 kDa to about 60 kDa. Other polymers suitable for use in the polymeric membrane compositions of the present disclosure may have molecular weight values falling within similar ranges.

In the polymeric membrane compositions of the present disclosure, an amine-free polyether arm may be appended to the heterocycle of at least a portion of the side chains in the heterocyclic polymer. For example, in the case of a polyvinylpyridine, the amine-free polyether arm may be covalently bonded to the pyridine ring, particularly via the pyridine nitrogen atom. The fraction of side chains in the polymeric membrane compositions with an amine-free polyether arm appended thereto may be about 0.1% or above of the available heterocycles in the heterocyclic polymer, or about 0.2% or above of the available heterocycles in the heterocyclic polymer, or about 0.3% or above of the available heterocycles in the heterocyclic polymer, or about 0.4% or above of the available heterocycles in the heterocyclic polymer, or about 0.5% or above of the available heterocycles in the heterocyclic polymer, or about 0.6% or above of the available heterocycles in the heterocyclic polymer, or about 0.7% or above of the available heterocycles in the heterocyclic polymer, or about 0.8% or above of the available heterocycles in the heterocyclic polymer, or about 0.9% or above of the available heterocycles in the heterocyclic polymer, or about 1.0% or above of the available heterocycles in the heterocyclic polymer, or about 1.2% or above of the available heterocycles in the heterocyclic polymer, or about 1.4% or above of the available heterocycles in the heterocyclic polymer, or about 1.6% or above of the available heterocycles in the heterocyclic polymer, or about 1.8% or above of the available heterocycles in the heterocyclic polymer, or about 2.0% or above of the available heterocycles in the heterocyclic polymer, or about 2.2% or above of the available heterocycles in the heterocyclic polymer, or about 2.4% or above of the available heterocycles in the heterocyclic polymer, or about 2.6% or above of the available heterocycles in the heterocyclic polymer, or about 2.8% or above of the available heterocycles in the heterocyclic polymer, or about 3.0% or above of the available heterocycles in the heterocyclic polymer, or about 3.5% or above of the available heterocycles in the heterocyclic polymer, or about 4.0% or above of the available heterocycles in the heterocyclic polymer, or about 4.5% or above of the available heterocycles in the heterocyclic polymer, or about 5.0% or above of the available heterocycles in the heterocyclic polymer, or about 5.5% or above of the available heterocycles in the heterocyclic polymer, or about 6.0% or above of the available heterocycles in the heterocyclic polymer, or about 6.5% or above of the available heterocycles in the heterocyclic polymer, or about 7.0% or above of the available heterocycles in the heterocyclic polymer, or about 7.5% or above of the available heterocycles in the heterocyclic polymer, or about 8.0% or above of the available heterocycles in the heterocyclic polymer, or about 8.5% or above of the available heterocycles in the heterocyclic polymer, or about 9.0% or above of the available heterocycles in the heterocyclic polymer, or about 9.5% or above of the available heterocycles in the heterocyclic polymer, or about 10% or above of the available heterocycles in the heterocyclic polymer. In more specific embodiments, an amine-free polyether arm may be appended to between about 0.1% and about 5% of the available heterocycles in the heterocyclic polymer, or between about 0.5% and about 4.5% of the available heterocycles in the heterocyclic polymer, or between about 1.0% and about 4.0% of the available heterocycles in the heterocyclic polymer, or between about 1.5% and about 3.0% of the available heterocycles in the heterocyclic polymer, or between about 1.5% and about 2.5% of the available heterocycles in the heterocyclic polymer.

In alternative embodiments, the amine-free polyether arm may be appended to a non-heterocycle side chain of the heterocyclic polymer, such as via covalent bonding to an optionally substituted phenyl group.

In some embodiments, at least a portion of the available heterocycles in the heterocyclic polymer may also have a crosslinker appended thereto. That is, in some embodiments, the polymeric membrane compositions of the present disclosure may further comprise a crosslinker appended to at least a portion of the one or more side chains and adjoining a first polymer backbone to a second polymer backbone. The crosslinker may be appended to the heterocyclic polymer in addition to the amine-free polyether arm. In some embodiments, the crosslinker may itself be a polyether, such as a polyethylene glycol or a copolymer of ethylene glycol and propylene glycol. Such crosslinkers are not limited in terms of the number of polyethylene glycol units that may be present. In some more specific embodiments, an amount of heterocycles functionalized with a crosslinker may be greater than an amount of heterocycles functionalized with an amine-free polyether arm. In other embodiments, an amount of heterocycles functionalized with a crosslinker may be less than an amount of heterocycles functionalized with an amine-free polyether arm. In illustrative embodiments, a bis-epoxide polyethylene glycol compound may be used to form a polymeric membrane composition bearing a crosslinker.

In more specific embodiments, the fraction of side chains that may have a crosslinker appended thereto may be about 0.1% or above of the available heterocycles in the heterocyclic polymer, or about 0.2% or above of the available heterocycles in the heterocyclic polymer, or about 0.3% or above of the available heterocycles in the heterocyclic polymer, or about 0.4% or above of the available heterocycles in the heterocyclic polymer, or about 0.5% or above of the available heterocycles in the heterocyclic polymer, or about 0.6% or above of the available heterocycles in the heterocyclic polymer, or about 0.7% or above of the available heterocycles in the heterocyclic polymer, or about 0.8% or above of the available heterocycles in the heterocyclic polymer, or about 0.9% or above of the available heterocycles in the heterocyclic polymer, or about 1.0% or above of the available heterocycles in the heterocyclic polymer, or about 1.2% or above of the available heterocycles in the heterocyclic polymer, or about 1.4% or above of the available heterocycles in the heterocyclic polymer, or about 1.6% or above of the available heterocycles in the heterocyclic polymer, or about 1.8% or above of the available heterocycles in the heterocyclic polymer, or about 2.0% or above of the available heterocycles in the heterocyclic polymer, or about 2.2% or above of the available heterocycles in the heterocyclic polymer, or about 2.4% or above of the available heterocycles in the heterocyclic polymer, or about 2.6% or above of the available heterocycles in the heterocyclic polymer, or about 2.8% or above of the available heterocycles in the heterocyclic polymer, or about 3.0% or above of the available heterocycles in the heterocyclic polymer, or about 3.5% or above of the available heterocycles in the heterocyclic polymer, or about 4.0% or above of the available heterocycles in the heterocyclic polymer, or about 4.5% or above of the available heterocycles in the heterocyclic polymer, or about 5.0% or above of the available heterocycles in the heterocyclic polymer, or about 5.5% or above of the available heterocycles in the heterocyclic polymer, or about 6.0% or above of the available heterocycles in the heterocyclic polymer, or about 6.5% or above of the available heterocycles in the heterocyclic polymer, or about 7.0% or above of the available heterocycles in the heterocyclic polymer, or about 7.5% or above of the available heterocycles in the heterocyclic polymer, or about 8.0% or above of the available heterocycles in the heterocyclic polymer, or about 8.5% or above of the available heterocycles in the heterocyclic polymer, or about 9.0% or above of the available heterocycles in the heterocyclic polymer, or about 9.5% or above of the available heterocycles in the heterocyclic polymer, or about 10% or above of the available heterocycles in the heterocyclic polymer. In more specific embodiments, a crosslinker may be appended to between about 1% and about 20% of the available heterocycles in the heterocyclic polymer, or between about 2% and about 10% of the available heterocycles in the heterocyclic polymer, or between about 3% and about 8% of the available heterocycles in the heterocyclic polymer, or between about 4% and about 9% of the available heterocycles in the heterocyclic polymer, or between about 5% and about 12% of the available heterocycles in the heterocyclic polymer.

Alternatively, in some embodiments, at least a portion of the non-heterocycle side chains of the heterocyclic polymer, such as an optionally substituted phenyl group, may have a crosslinker appended thereto.

According to various embodiments, the amine-free polyether arm may be bound to the polymer backbone in the polymeric membrane compositions disclosed herein via a heteroatom within at least a portion of the heterocycles in the one or more side chains of the heterocyclic polymer. Alternative embodiments may include those in which the amine-free polyether arm is bound to the polymer backbone via a carbon atom of at least a portion of the heterocycles in the one or more side chains and/or via a carbon atom in an optionally substituted phenyl group in the polymer backbone. In more specific embodiments, the amine-free polyether arm may be bound to the polymer backbone via a heterocyclic or heteroaromatic nitrogen atom within the one or more side chains. For example, in the case of the polymer backbone being polyvinylpyridine or a copolymer thereof, the amine-free polyether arm may be appended to a side chain via the pyridine nitrogen atom. When functionalized with an amine-free polyether arm or a crosslinker, the pyridine nitrogen atom is in quaternized form.

Accordingly, in more specific embodiments, polymeric membrane compositions of the present disclosure, in which the amine-free polyether arm is bonded to a pyridine nitrogen atom, may have repeat units defined by Formulas 2 and 3 below, wherein variables a, b and Q are defined as above, c is a positive

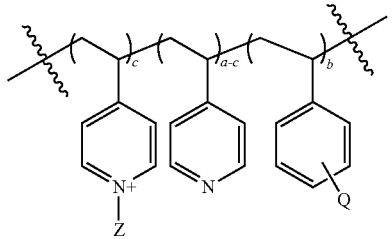

Formula 2

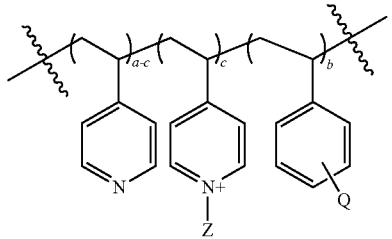

Formula 3 integer not greater than a, and Z is an amine-free polyether arm, a crosslinker, or any combination thereof. When both an amine-free polyether arm and a crosslinker are present, the polymeric membrane compositions may have a structure defined by one or more of Formulas 4-7, wherein variables a, b and Q are Formula 4
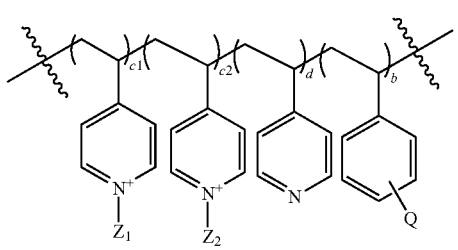

Formula 5
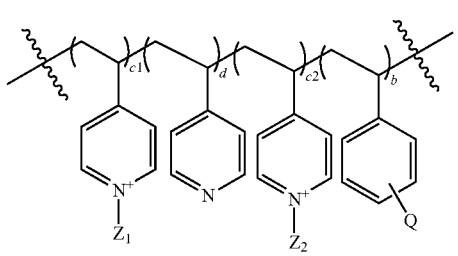

Formula 6
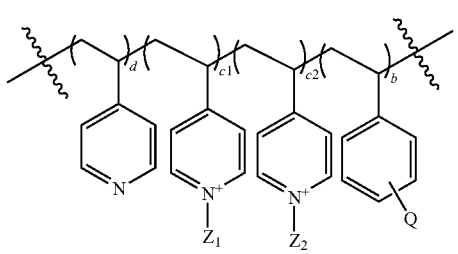

Formula 7
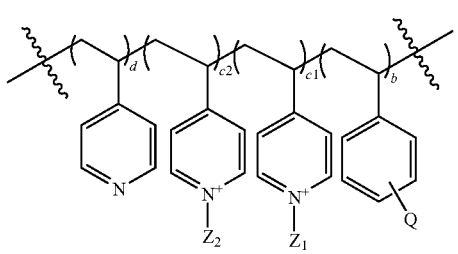

defined as above, c1 and c2 are positive integers whose sum is not greater than a, d is specified by Equation 1, $Z_1$ is an amine-free polyether arm, and $Z_2$ is a $$d = a - c1 - c2 \qquad \text{(Equation 1)}$$

crosslinker. As such, the heteroaromatic (pyridine) rings in the heterocyclic polymer may be functionalized with $Z_1$ and $Z_2$ in any combination or pattern in the various polymeric membrane composition embodiments of the present disclosure. That is, the repeat units defined by Formulas 2-7 may be present in any combination with one another in defining a heterocyclic polymer suitable for incorporation in the polymeric membrane compositions of the present disclosure.

In other specific embodiments, polymeric membrane compositions having the amine-free polyether arm bonded to a pyridine moiety, but not via the pyridine nitrogen atom, may be defined by Formulas 8 and 9 below, wherein variables a, b, c and Q and Z are defined as above.

Formula 8
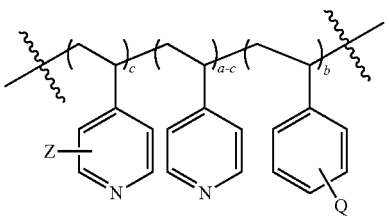

Formula 9
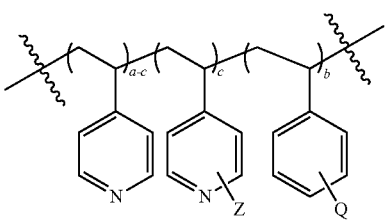

Optionally, any of the pyridine nitrogen atoms in Formulas 8 and 9 may be quaternized with an alkyl group (e.g., through reaction with an alkyl halide) when the amine-free polyether arm is bonded to a carbon atom of the pyridine. Any unsubstituted carbon atoms in the pyridine groups may be bonded to an amine-free polyether arm and/or a crosslinker according to the embodiments described herein. When both an amine-free polyether arm and a crosslinker are present, the amine-free polyether arm and the crosslinker may be present upon the same pyridine group or different pyridine groups.

In various embodiments, the amine-free polyether arm may comprise at least one polyethylene oxide block and at least one polypropylene oxide block. The amine-free polyether arm may comprise a diblock arrangement of polyethylene oxide and polypropylene oxide, according to some embodiments. That is, in some embodiments, the amine-free polyether arm may comprise, in order an alkyl spacer or a hydroxy-functionalized alkyl spacer, a polyethylene oxide block and a polypropylene oxide block, and in other embodiments, the amine-free polyether arm may comprise, in order, an alkyl spacer or a hydroxy-functionalized alkyl spacer, a polypropylene oxide block and a polyethylene oxide block. In other more specific embodiments, the amine-free polyether arm may comprise, in order, an alkyl spacer or a hydroxy-functionalized alkyl spacer, a first polyethylene oxide block, a polypropylene oxide block, and a second polyethylene oxide block (i.e., an A-B-A repeat pattern). In still other more specific embodiments, the amine-free polyether arm may comprise, in order, an alkyl spacer or a hydroxy-functionalized alkyl spacer, a first polypropylene oxide block, a polyethylene oxide block, and a second polypropylene oxide block (i.e., a B-A-B repeat pattern). The alkyl spacer or the hydroxy-functionalized alkyl spacer may be bound to a heterocyclic or heteroaromatic nitrogen atom in a side chain of the polymer backbone, according to various embodiments. Alternative bonding to any of the carbon atoms of a heterocyclic side chain or any of the carbon atoms of a side chain phenyl group are also possible in some instances. The alkyl spacer or the hydroxy-functionalized alkyl spacer may also be bound to the first polyethylene oxide block in the amine-free polyether arm, according to various embodiments, such as through a terminal ether linkage. The second polyethylene oxide block may be terminated by a methoxy group, according to some embodiments. Alternately, the alkyl spacer of the hydroxy-functionalized alkyl spacer may also be bound to a first polypropylene oxide block in the amine-free polyether arm, and a second polypropylene oxide block may be terminated by a methoxy group, according to some embodiments.

Accordingly, in various embodiments of the present disclosure, the amine-free polyether arm may have a structure defined by Formulas 10 or 11 below,

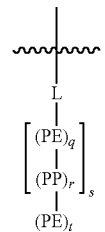

Formula 10

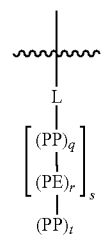

Formula 11 wherein PE represents a polyethylene oxide block, PP represents a polypropylene oxide block, and L is a spacer group. Suitable spacer groups may include, but are not limited to alkyl, hydroxy-functionalized alkyl, carbonyl, carboxylic ester, carboxamide, and the like. Variables q, r, s, and t are positive integers defining the number of monomer units in each block and the number of times the blocks are repeated, with the proviso that in diblock arrangements of polyethylene oxide and polypropylene oxide applicable to Formulas 10 and 11, variable t may be 0. In Formula 10 with t≠0, the terminal polyethylene oxide monomer unit may be substituted with alkoxy group, such as a methoxy group. Likewise, in Formula 11 with t≠0, the terminal polypropylene oxide monomer unit may be substituted with alkoxy group, such as a methoxy group. Diblock arrangements associated with Formulas 10 and 11, in which t=0, may similarly have alkoxy group termination. According to some embodiments, variable q is an integer ranging between about 2 and about 50 or between about 6 and about 20, variable r is an integer ranging between about 2 and about 60 or between about 10 and about 40, and variable t is an integer ranging between about 2 and about 50 or between about 10 and about 30. According to some or other various embodiments, variable s is an integer ranging between 1 and about 20 or between 1 and about 10. In some embodiments, variable s is equal to 1. Diblock arrangements of polyethylene oxide and polypropylene oxide may include variables q and r within the same ranges as above, but with variable s equal to 1 and variable t equal to 0.

In more specific embodiments of the present disclosure, the amine-free polyether arm may have a structure defined by Formula 12, wherein variable w

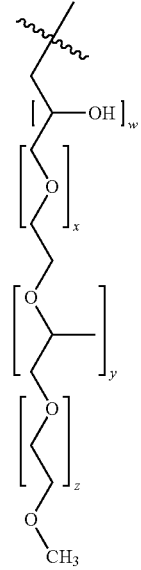

Formula 12 is 0 or 1, variable x is an integer ranging between about 4 and about 24 or between about 6 and about 20, variable y is an integer ranging between about 8 and about 60 or between about 10 and about 40, and variable z is an integer ranging between about 6 and about 36 or between about 10 and about 30. Alternately, variable z may be 0 in a diblock arrangement, with the other variables residing in the same ranges. In more specific embodiments, variable x may range between about 8 and about 16 or between about 9 and about 12, variable y may range between about 10 and about 32, or between about 16 and about 30, or between about 12 and about 20, and variable z may range between about 10 and about 20 or between about 14 and about 18. In still other more specific embodiments, x may be 10, y may be 20 and z may be 14; or x may be 12, y may be 16 and z may be 16; or x may be 14, y may be 12 and z may be 18. In some embodiments, x may be less than z, such that the second polyethylene oxide block is longer (larger) than the first polyethylene oxide block.

In some embodiments, the ratio of (x+z):y in Formula 12 may be at least about 1.4:1, or at least about 1.7:1, or at least about 2:1, or at least about 2.5:1, or at least about 3:1, or at least about 3.5:1. In more specific embodiments, the ratio of (x+z):y in Formula 12 may range between about 1.4:1 to about 5:1, or between about 1.7:1 to about 3.2:1, or between about 2.2:1 to 3.0:1, or between about 2.6:1 and about 2.9:1, or between about 3:1 and about 5:1.

In some embodiments of the present disclosure, the amine-free polyether arm may have a structure defined by Formula 13, wherein variable w

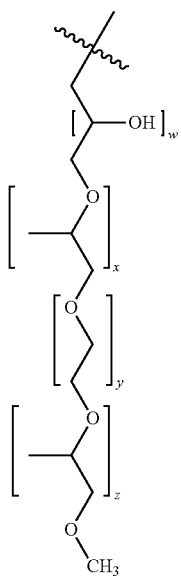

Formula 13

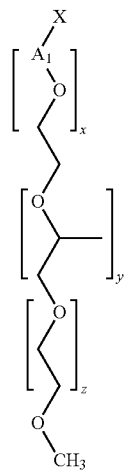

Formula 14

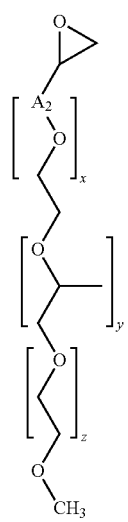

Formula 15 is 0 or 1, variable x is an integer ranging between about 4 and about 24 or between about 6 and about 20, variable y is an integer ranging between about 8 and about 60 or between about 10 and about 40, and variable z is an integer ranging between about 6 and about 36 or between about 10 and about 30. Alternately, variable z may be 0 in a diblock arrangement, with the other variables residing in the same ranges. In more specific embodiments, variable x may range between about 6 and about 16 or between about 9 and about 12, variable y may range between about 10 and about 40, or between about 16 and about 30, or between about 14 and about 32, and variable z may range between about 8 and about 20 or between about 12 and about 16.

The amine-free polyether arms described herein may become bonded to a heterocycle in the side chain of a heterocyclic polymer by way of a reactive functionality in an amine-free polyether arm precursor. Suitable reactive functionalities may include a halogen or an epoxide, for example, either of which may be reacted via nucleophilic attack from the side chain of the heterocyclic polymer. Halogen-functionalized amine-free polyether arm precursors lead to amine-free polyether arms in which n is 0 (i.e., the spacer is an alkyl group), whereas epoxide-functionalized amine-free polyether arm precursors lead to amine-free polyether arms in which n is 1 (i.e., the spacer is a propyl group bearing a secondary alcohol). In more specific embodiments, alkyl spacers resulting from halogen-functionalized amine-free polyether arm precursors may include alkyl groups that are straight- or branched-chain and contain 2 to about 20 carbon atoms. In more specific embodiments, halides that may be suitably included in halogen-functionalized amine-free polyether arm precursors include chloride or bromide, with bromide being chosen in more particular embodiments.

Formulas 14 and 15 show structures of illustrative amine-free polyether arm precursors that may be suitably reacted with a heterocyclic polymer to form certain polymeric membrane compositions disclosed herein, in which variable x, y, and z are defined as above.

In Formula 14, variable $A_1$ represents an alkyl group having between 2 and about 20 carbon atoms, such as between 2 and about 4 carbon atoms, or between 2 and about 6 carbon atoms, or between 2 and about 8 carbon atoms, and X is a halide, such as chloride or bromide. The alkyl group of $A_1$ may be branched- or straight-chain and optionally contain heteroatom substitution. Halide X may be a primary alkyl halide, according to various embodiments. In Formula 15, variable $A_2$ represents an alkyl group having between 1 and about 10 carbon atoms, such as 1 carbon atom, 2 carbon atoms, 3 carbon atoms, or 4 carbon atoms. In some embodiments, the alkyl group of $A_2$ may be straight-chain, and in other embodiments, the alkyl group $A_2$ may contain branching.

In more specific embodiments, suitable amine-free polyether arm precursors for forming the polymeric membrane compositions disclosed herein may include those shown in Formulas 16 and 17, in which the variables are defined as above.

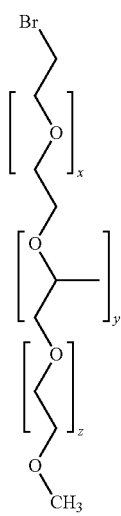

Formula 16

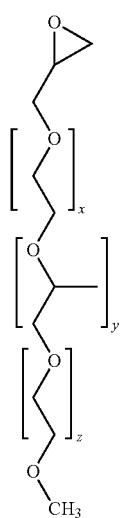

Formula 17

In some embodiments, a sulfonate-containing arm may be appended to at least a portion of the one or more side chains in the heterocyclic polymers disclosed herein. The sulfonate-containing arm may be present in combination with any of the amine-free polyether arms disclosed herein and in any suitable ratio. In some embodiments, the polymeric membrane compositions disclosed herein may comprise a higher quantity of amine-free polyether arms than sulfonate-containing arms.

According to more specific embodiments, a sulfonate-containing arm may be appended to the heterocycle of a heterocyclic polymer via an alkyl group. The alkyl group may contain between 1 and about 6 carbon atoms, or between 2 and about 4 carbon atoms, according to various embodiments. Suitable reagents for introducing a sulfonate-containing arm to the heterocyclic polymers disclosed herein may include halosulfonic acid compounds such as chloromethanesulfonic acid, bromoethanesulfonic acid, or the like, or cyclic sulfonates (sultones).

In some embodiments, an amine-free polyether arm comprising a single type of repeating ether unit may be appended to at least a portion of the one or more side chains in the heterocyclic polymers disclosed herein. Such amine-free polyether arms may be present in combination with a sulfonate-containing arm and/or an amine-free polyether arm bearing two or more different types of ether unit blocks, such as those described by Formulas 10-13.

According to more specific embodiments, an amine-free polyether arm comprising a single type of repeating ether unit may be a polyethylene oxide arm or a polypropylene oxide arm. In more particular embodiments, the amine-free polyether arm may be an amine-free polyethylene oxide arm appended, via an alkyl spacer or a hydroxy-functionalized alkyl spacer, to the heterocycle of at least a portion of the one or more side chains. Between about 8 to about 25, or between about 10 to about 22, or between about 12 to about 20 repeating ether units may be present in the amine-free polyether arm comprising a single type of repeating ether unit. The repeating polyethylene oxide or polypropylene oxide ether units may be appended to the one or more side chains of the heterocyclic polymer via an alkyl group or a hydroxyl-functionalized alkyl group. The alkyl group may contain between 1 and about 6 carbon atoms, or between 2 and about 4 carbon atoms, according to various embodiments. The hydroxy-functionalized alkyl group may contain 3 carbon atoms with a hydroxyl group on the central carbon atom. An alkoxy group, particularly a methoxy group, may terminate the amine-free polyether arm opposite the point of attachment to the heterocyclic polymer. Such amine-free polyether arms may be introduced to the heterocyclic polymer by reacting a polyether terminated with either an alkyl halide or an epoxide with the heterocyclic polymer.

In some embodiments, the polymeric membrane compositions of the present disclosure may be crosslinked, as referenced in brief above. Crosslinked polymers suitable for incorporation in the polymeric membrane compositions may comprise a crosslinker that connects two or more polymer backbones together with one another (intermolecular crosslinking) or different portions of the same polymer backbone together with one another (intramolecular crosslinking). A "crosslinking agent" containing two or more reactive functionalities may promote such crosslinking. Once crosslinking has occurred, a portion of the crosslinking agent may remain as a crosslinker, either intermolecularly or intramolecularly linking polymer chain(s) to one another.

In some embodiments, suitable crosslinking agents may comprise a polyetherimine and a glycidyl ether, such as diglycidyl ether. This combination of reagents forms crosslinks containing an amine group. In other embodiments, suitable crosslinking agents may comprise a polyether and a glycidyl ether, such as diglycidyl ether, which leads to crosslinks lacking an amine group. In more particular embodiments, suitable crosslinking agents for forming amine-free crosslinks may comprise a polyethylene oxide/polypropylene oxide copolymer and a glycidyl ether, such as diglycidyl ether, or polyethylene oxide and a glycidyl ether, such as diglycidyl ether.

In some or other embodiments, suitable crosslinking agents may comprise a polyethylene oxide block having a terminal propylene oxide unit at each end of the polyethylene oxide block. Such a crosslinking agent may have the structure shown in Formula 18, wherein variable n is a positive integer ranging Formula 18

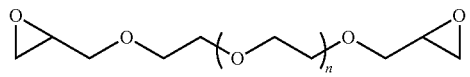

between about 10 and about 500, or between about 10 and about 100, or between about 10 and about 50, or between about 12 and about 36, or between about 12 and about 30, or between about 12 and about 28, or between about 12 and about 26, or between about 12 and about 24, or between about 12 and about 22, or between about 12 and about 20, or between about 14 and about 28, or between about 14 and about 24, or between about 16 and about 30, or between about 16 and about 24. As can be appreciated by one having ordinary skill in the art, the crosslinking agent of Formula 18 reacts to form a crosslink in which the polyethylene oxide block is bound to a polymer backbone on each end via a hydroxy-functionalized alkyl group. Specifically, the crosslinking agent of Formula 18 produces the crosslinker of Formula 19 upon nucleophilic opening of the epoxide ring in each terminal propylene oxide unit, wherein n is defined as above.

Formula 19

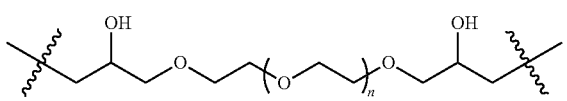

Accordingly, in more specific embodiments of the present disclosure, suitable crosslinks may comprise at least one polyethylene oxide block that is bound on opposing ends to a first heterocycle of first polymer backbone and a second heterocycle of a second polymer backbone, each via a hydroxy-functionalized alkyl group. In such embodiments, the manner of crosslinking is intermolecular. In some or other embodiments of the present disclosure, such crosslinking agents may be bound on opposing ends to first and second heterocycles within the same polymer backbone, each via a hydroxyl-functionalized alkyl group, in which case the manner of crosslinking is intramolecular.

Crosslinking agents having additional epoxide groups may also be used in some embodiments, such as the illustrative tris-epoxide compound shown in Formula 20. Such crosslinking agents may lead to the formation of crosslinks between more than two polymer backbones.

Formula 20

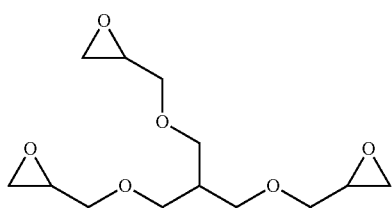

Optionally, such crosslinking agents may be further reacted with a polyethylene glycol, a polypropylene glycol, or an ethylene glycol/propylene glycol copolymer to form a given crosslink.

Advantageously, the polymeric membrane compositions of the present disclosure may form temperature-insensitive membranes, according to various embodiments. As used herein, the term "temperature-insensitive" refers to the condition of a parameter of interest varying in a clinically or statistically insignificant manner as a function of temperature over a given range. In more specific embodiments, temperature-insensitive membranes of the present disclosure may be temperature-insensitive with respect to the analyte permeability, particularly glucose. Other analytes may also exhibit temperature-insensitive membrane permeability, with the rate of permeation being the same as or different than that of glucose. As such, the limited variation in analyte permeability may lead to little or no change in sensor response when assaying a fixed concentration of analyte over a given temperature range at which the polymeric membrane composition is temperature-insensitive.

In more specific embodiments, the polymeric membrane compositions of the present disclosure may be temperature-insensitive toward analyte permeability (e.g., glucose) over a temperature range of about 10° C. to about 70° C., or about 15° C. to about 65° C., or about 20° C. to about 60° C., or about 25° C. to about 50° C., or about 15° C. to about 45° C., or about 15° C. to about 40° C. or about 20° C. to about 45° C., or about 25° C. to about 40° C. In some or other more specific embodiments, the variation of the polymeric membrane compositions toward analyte permeability (e.g., glucose) may be about 10% or less over the temperature range, or about 5% or less over the temperature range, or about 2% or less over the temperature range, or about 1% or less over the temperature range, or about 0.5% or less over the temperature range, or about 0.1% or less over the temperature range, or about 0.05% or less over the temperature range, or about 0.01% or less over the temperature range. Within a subrange of the broader temperature range (e.g., about 15° C. to about 45° C.), the variation of the polymeric membrane compositions toward analyte permeability may be about 2% or less or about 1% or less over a given 5° C. temperature increment. Determination of the variation of the polymeric membrane compositions toward analyte permeability may be ascertained by measuring the difference in sensor response over a specified temperature range at a fixed concentration of analyte (see FIG. 4 herein).

The polymeric membrane compositions described herein may be further characterized in terms of their biocompatibility properties. In various embodiments, the polymeric membrane compositions may be characterized as having a cytotoxicity score of 2, or a cytotoxicity score of 1, or a cytotoxicity score of 0. Such cytotoxicity scores may be present in combination with characteristics such as lack of hemolysis, mutagenicity, irritation, and similar properties. In some embodiments, the polymeric membrane compositions of the present disclosure meet or exceed ISO 10993-1 standards. ISO 10993-1 standards for tissue-implanted devices include clinical lack of the following: cytotoxicity, sensitization, irritation or intracutaneous reactivity, acute systemic toxicity, pyrogenicity, subacute or subchronic toxicity, genotoxicity, and implantation issues.

The polymeric membrane compositions disclosed hereinabove may be present in an analyte sensor, according to various embodiments. Accordingly, analyte sensors of the present disclosure may comprise a sensing region (i.e., an active portion of the sensor), and a polymeric membrane composition overlaying the sensing region. The polymeric membrane composition may comprise a polymer backbone comprising one or more side chains that comprise a heterocycle, and an amine-free polyether arm appended, via an alkyl spacer or a hydroxyl-functionalized alkyl spacer, to the heterocycle of at least a portion of the one or more side chains. Any of the polymeric membrane compositions may be utilized in conjunction with an analyte sensor, as discussed further herein.

In some embodiments, the sensing region of the analyte sensors of the present disclosure may comprise an enzyme. The enzyme may catalyze a reaction that consumes an analyte of interest or produces a product that is detectable by the analyte sensor. The enzyme may be covalently bonded to a polymer comprising at least a portion of the sensing region, according to some embodiments. Choice of a particular enzyme may be dictated by the analyte of interest to be detected. Glucose oxidase or glucose dehydrogenase (e.g., pyrroloquinoline quinone (PQQ), dependent glucose dehydrogenase, flavine adenine dinucleotide (FAD) dependent glucose dehydrogenase, or nicotinamide adenine dinucleotide (NAD) dependent glucose dehydrogenase) may be used when the analyte of interest is glucose. Lactate oxidase or lactate dehydrogenase may be used when the analyte of interest is lactate. Laccase may be used when the analyte of interest is oxygen or when oxygen is generated or consumed in response to a reaction of the analyte. Other enzymes may be employed similarly for detecting other analytes of interest, as will be appreciated by one having ordinary skill in the art and the benefit of the present disclosure. Any of the substrates acted upon by the foregoing enzymes or other enzymes may be an analyte suitable for analysis with the analyte sensors disclosed herein.

Additional details of illustrative analyte sensors that may be used in conjunction with the polymeric membrane compositions of the present disclosure are discussed in further detail hereinafter. It is to be appreciated, however, that analyte sensors having different architectures and components other than those expressly disclosed herein may be suitably used as well.

FIG. 1 shows a diagram of an illustrative analyte monitoring system that may incorporate an analyte sensor of the present disclosure. As shown, analyte monitoring system 100 includes sensor control device 102 and reader device 120 that are configured to communicate with one another over a local communication path or link, which may be wired or wireless, uni- or bi-directional, and encrypted or non-encrypted. Reader device 120 may also be in communication with remote terminal 170 and/or trusted computer system 180 via communication path(s)/link(s) 141 and/or 142, respectively, which also may be wired or wireless, uni- or bi-directional, and encrypted or non-encrypted. Any suitable electronic communication protocol may be used for each of the local communication paths or links. Reader device 120 may comprise display 122 and optional input component 121.

Sensor control device 102 includes sensor housing 103, which may include circuitry and a power source for operating sensor 104. Sensor 104 protrudes from sensor housing 103 and extends through adhesive layer 105. Suitable adhesives for inclusion in adhesive layer 105 will be familiar to one having ordinary skill in the art.

Sensor 104 is adapted to be at least partially inserted into a tissue of interest, such as the dermal layer of the skin. Sensor 104 may comprise a sensor tail of sufficient length for insertion to a desired depth in a given tissue. The sensor tail may comprise a sensing region that is active for sensing, and may comprise an enzyme, according to one or more embodiments. The sensing region includes a polymeric membrane composition of the present disclosure, according to various embodiments. One or more analyte levels may be determined using sensor 104 and undergo communication to reader device 120, according to one or more embodiments. The analyte may be monitored in any biological fluid such as dermal fluid, plasma, blood, lymph, or the like. Analytes that may be monitored are not considered to be particularly limited. In certain embodiments, the analyte may be glucose. Other analytes of interest with respect to human physiology may include, for example, lactate, oxygen, pH, A1c, ketones, drug levels, and the like. Any of these analytes may exhibit temperature-insensitive permeability through the polymeric membrane compositions disclosed herein. Both single analytes and any combination of the foregoing analytes may be assayed.

An introducer may be present transiently to promote introduction of sensor 104 into a tissue. In illustrative embodiments, the introducer may comprise needle a 109. It is to be recognized that other types of introducers, such as sheaths or blades, may be present in alternative embodiments. More specifically, the needle or similar introducer may transiently reside in proximity to sensor 104 prior to insertion and then be withdrawn afterward. While present, the needle or other introducer may facilitate insertion of sensor 104 into a tissue by opening an access pathway for sensor 104 to follow. For example, the needle may facilitate penetration of the epidermis as an access pathway to the dermis to allow implantation of sensor 104 to take place, according to one or more embodiments. After opening the access pathway, the needle or other introducer may be withdrawn so that it does not represent a sharps hazard. In illustrative embodiments, the needle may be solid or hollow, beveled or non-beveled, and/or circular or non-circular in cross-section. In more particular embodiments, the needle may be comparable in cross-sectional diameter and/or tip design to an acupuncture needle, which may have a cross-sectional diameter of about 250 microns. It is to be recognized, however, that suitable needles may have a larger or smaller cross-sectional diameter if needed for particular applications. In alternative embodiments, needle 109 or similar introducers may be absent, provided sensor 104 is sufficiently robust to penetrate a tissue and establish communication with a bodily fluid of interest.

In some embodiments, a tip of the needle may be angled over the terminus of sensor 104, such that the needle penetrates a tissue first and opens an access pathway for sensor 104. In other illustrative embodiments, sensor 104 may reside within a lumen or groove of the needle 109, with the needle similarly opening an access pathway for sensor 104. In either case, the needle is subsequently withdrawn after facilitating insertion.

It is to be recognized that analyte monitoring system 100 may comprise additional features and functionality that are not necessarily described herein in the interest of brevity. Accordingly, the foregoing description of analyte monitoring system 100 should be considered illustrative and non-limiting in nature.

Analyte sensors of the present disclosure may comprise two-electrode or three-electrode detection motifs, according to various embodiments. Three-electrode motifs may comprise a working electrode, a counter electrode, and a reference electrode. Two-electrode motifs may comprise a working electrode and a second electrode, in which the second electrode functions as both a counter electrode and a reference electrode (i.e., a counter/reference electrode). In both two-electrode and three-electrode detection motifs, the sensing region of the analyte sensors described herein may be in contact with the working electrode. In various embodiments, the various electrodes may be at least partially stacked upon one another, as described in further detail hereinafter. In alternative embodiments, the various electrodes may be spaced apart from one another upon the insertion tail of an analyte sensor.

Figure 2:
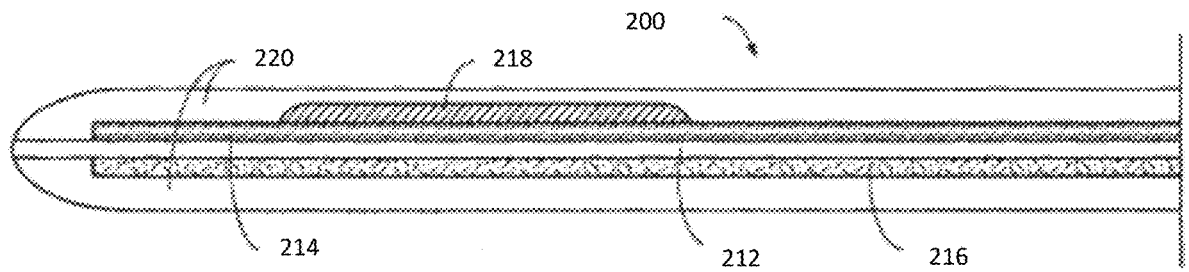
FIG. 2 shows a diagram of an illustrative two-electrode sensor configuration compatible with the disclosure herein.

FIG. 2 shows a diagram of an illustrative two-electrode sensor configuration compatible with the disclosure herein. As shown, analyte sensor 200 comprises substrate 212 disposed between working electrode 214 and counter/reference electrode 216. Alternately, working electrode 214 and counter/reference electrode 216 may be located upon the same side of substrate 212 with a dielectric material interposed in between. Sensing region 218 is disposed as at least one spot on at least a portion of working electrode 214. Membrane 220 overcoats at least sensing region 218 and may optionally overcoat some or all of working electrode 214 and/or counter/reference electrode 216 in some embodiments. One or both faces of sensor 200 may be overcoated with membrane 220. Membrane 220 may comprise any of the polymeric membrane compositions disclosed herein.

Figure 3A:
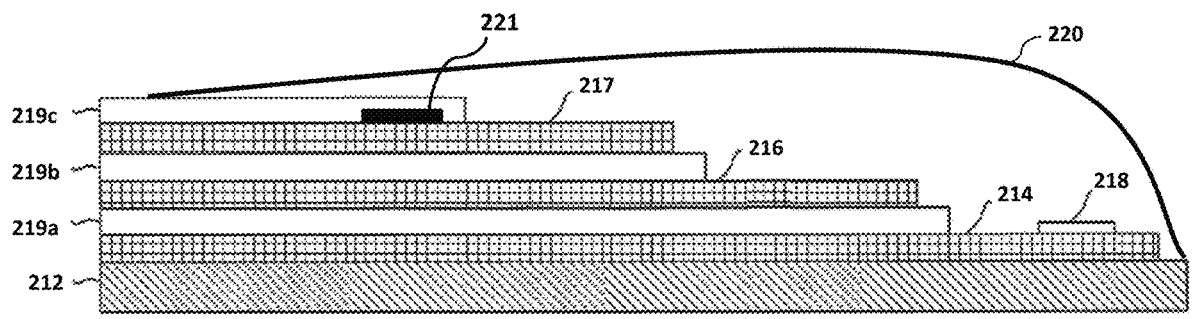
FIG. 3A shows a diagram of an illustrative three-electrode sensor configuration compatible with the disclosure herein.
Figure 3B:
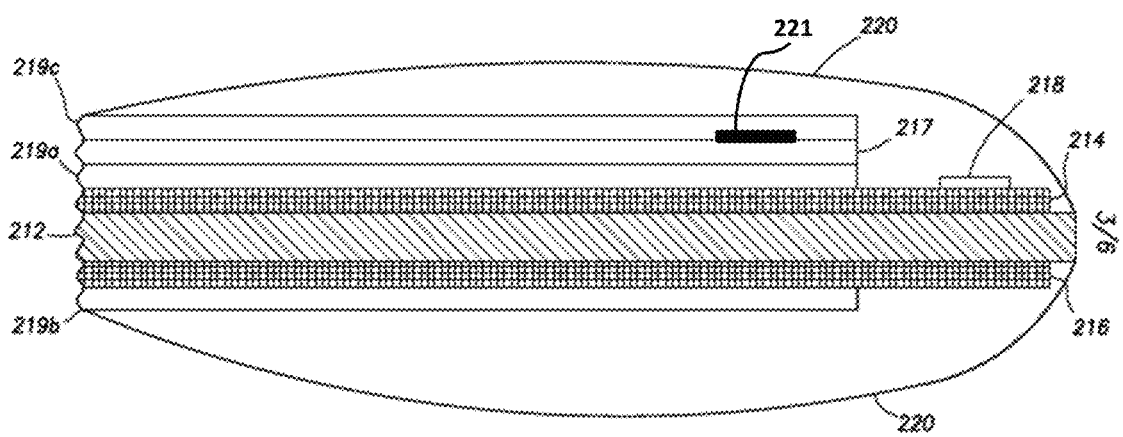
FIG. 3B shows a diagram of another configuration of an illustrative three-electrode sensor compatible with the disclosure herein.

Three-electrode sensor configurations may be similar to analyte sensor 200, except for the inclusion of an additional electrode (FIGS. 3A and 3B). With an additional electrode 217, counter/reference electrode 216 then functions as either a counter electrode or a reference electrode, and the additional electrode 217 (FIGS. 3A and 3B) fulfills the other function not otherwise fulfilled. The additional electrode 217 may be disposed upon either working electrode 214 or counter/reference electrode 216, with a separating layer of dielectric material in between. For example, as depicted in FIG. 3A dielectric layers 219a, 219b and 219c separate electrodes 214, 216 and 217 from one another. Alternately, at least one of electrodes 214, 216 and 217 may be located upon the opposite face of substrate 212 (FIG. 3B). Thus, in some embodiments, electrode 214 (working electrode) and electrode 216 (counter electrode) may be located upon opposite faces of substrate 212, with electrode 217 (reference electrode) being located upon one of electrodes 214 or 216 and spaced apart therefrom with a dielectric material. Conducting layer 222, such as a silver/silver chloride reference, may be located upon electrode 217 (reference electrode), according to some embodiments. As with sensor 200 shown in FIG. 2, sensing region 218 may comprise a single spot or multiple spots configured for detecting an analyte of interest.

Additional electrode 217 may optionally be overcoated with membrane 220 in some embodiments. Although FIGS. 3A and 3B have depicted all of electrodes 214, 216 and 217 as being overcoated with membrane 220, it is to be recognized that it is only necessary for sensing region 218 to be overcoated in order to realize the benefits described herein. As such, the configurations shown in FIGS. 3A and 3B should be understood as being non-limiting of the embodiments disclosed herein. As in two-electrode configurations, one or both faces of sensor 200 may be overcoated with membrane 220.

When coated upon sensing region 218, membrane 220 may have a thickness ranging between about 0.1 microns and about 1000 microns, or between about 1 microns and about 500 microns, or between about 10 microns and about 100 microns.

In some embodiments, sensing region 218 may comprise a polymer that is bonded to glucose oxidase or another enzyme and a low-potential osmium complex electron transfer mediator, as disclosed in, for example, U.S. Pat. No. 6,134,461, which is incorporated herein by reference in its entirety. Other suitable electron transfer mediators may comprise metal compounds or complexes of ruthenium, iron, or cobalt, for example. Suitable ligands for the metal complexes may include, for example, bidentate or higher denticity ligands such as, for example, a bipyridine, biimidazole, or pyridyl(imidazole). Other suitable bidentate ligands may include, for example, amino acids, oxalic acid, acetylacetone, diaminoalkanes, or o-diaminoarenes. Any combination of monodentate, bidentate, tridentate, tetradentate, or higher denticity ligands may be present in the metal complex to achieve a full coordination sphere.

The enzyme in sensing region 218 may be covalently bonded to a polymer or other suitable matrix via a crosslinking agent. Suitable crosslinking agents for reaction with free amino groups in the enzyme (e.g., with the free amine in lysine) may include crosslinking agents such as, for example, polyethylene glycol diglycidylether (PEGDGE) or other polyepoxides, cyanuric chloride, N-hydroxysuccinimide, imidoesters, or derivatized variants thereof. Suitable crosslinking agents for reaction with free carboxylic acid groups in the enzyme may include, for example, carbodiimides.

A variety of approaches may be employed to determine the concentration of an analyte using analyte sensor 200. For example, the concentration of the analyte may be monitored using any of coulometric, amperometric, voltammetric, or potentiometric electrochemical detection techniques.

Embodiments disclosed herein include:

A. Polymeric Membrane Compositions. The polymeric membrane compositions comprise: a polymer backbone comprising one or more side chains that comprise a heterocycle; and an amine-free polyether arm appended, via an alkyl spacer or a hydroxy-functionalized alkyl spacer, to the heterocycle of at least a portion of the one or more side chains.

B. Analyte sensors. The analyte sensors comprise: a sensing region; and a polymeric membrane composition overlaying the sensing region; wherein the polymeric membrane composition comprises a polymer backbone comprising one or more side chains that comprise a heterocycle, and an amine-free polyether arm appended, via an alkyl spacer or a hydroxy-functionalized alkyl spacer, to the heterocycle of at least a portion of the one or more side chains.

C. Polymeric membrane compositions having temperature insensitivity to glucose or other potential analytes. The polymeric membrane compositions are temperature-insensitive to at least glucose permeability over a temperature range of about 15° C. to about 45° C. and meet or exceed ISO 10993-1 standards.

Each of embodiments A and B may have one or more of the following additional elements in any combination Element 1: wherein the polymer backbone comprises a polyvinylpyridine or a polyvinylimidazole.

Element 2: wherein the polymer backbone comprises a copolymer of vinylpyridine and styrene.

Element 3: wherein the amine-free polyether arm comprises at least one polyethylene oxide block and at least one polypropylene oxide block, the amine-free polyether arm being bound to a heterocyclic or heteroaromatic nitrogen atom in a side chain of the polymer backbone.

Element 4: wherein the amine-free polyether arm has a structure of

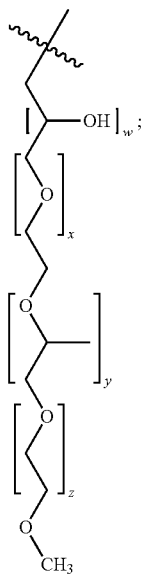

wherein w is 0 or 1, x ranges between about 4 and about 24, y ranges between about 8 and about 60, and z ranges between about 6 and about 36.

Element 5: wherein x ranges between about 8 and about 16, y ranges between about 10 and about 32, and z ranges between about 10 and about 20.

Element 6: wherein x≤z.

Element 7: wherein a ratio of (x+z):y is at least about 1.7:1.

Element 8: wherein a ratio of (x+z):y ranges between about 1.7:1 and about 5:1.

Element 9: wherein the polymeric membrane composition further comprises a sulfonate-containing arm appended to at least a portion of the one or more side chains.

Element 10: wherein the polymeric membrane composition further comprises a crosslinker appended to at least a portion of the one or more side chains and adjoining a first polymer backbone to a second polymer backbone.

Element 11: wherein the sensing region comprises an enzyme.

Element 12: wherein the polymeric membrane composition further comprises: an amine-free polyethylene oxide arm appended, via an alkyl spacer or a hydroxy-functionalized alkyl spacer, to the heterocycle of at least a portion of the one or more side chains.

By way of non-limiting example, exemplary combinations applicable to A and B include:

The composition of A in combination with elements 1 and 2; 1 and 3; 1 and 4; 1, 4 and 5; 1, 4 and 6; 1, 4, 5 and 6; 1, 4 and 7; 1, 4, 5 and 7; 1, 4 and 8; 1, 4, 5 and 8; 1 and 9; 1 and 10; 1 and 12; 1, 9 and 10; 2 and 3; 2 and 4; 2, 4 and 5; 2, 4 and 6; 2, 4, 5, and 6; 2, 4 and 7; 2, 4, 5 and 7; 2, 4 and 8; 2, 4, 5 and 8; 2 and 9; 2 and 10; 2, 9 and 10; 3 and 4; 3, 4 and 5; 3, 4 and 6; 3, 4, 5 and 6; 3, 4 and 7; 3, 4, 5 and 7; 3, 4 and 8; 3, 4, 5 and 9; 3 and 9; 3 and 10; 3, 9 and 10; 4 and 5; 4 and 6; 4, 5 and 6; 4 and 7; 4, 5 and 7; 4 and 8; 4, 5 and 8; 4 and 9; 4 and 10; 4, 9 and 10; 4 and 12; 9 and 10; 10 and 12; and 11 and 12. The analyte sensor of B in combination with elements 1 and 2; 1 and 3; 1 and 4; 1, 4 and 5; 1, 4 and 6; 1, 4, 5 and 6; 1, 4 and 7; 1, 4, 5 and 7; 1, 4 and 8; 1, 4, 5 and 8; 1 and 9; 1 and 10; 1, 9 and 10; 1 and 12; 2 and 3; 2 and 4; 2, 4 and 5; 2, 4 and 6; 2, 4, 5, and 6; 2, 4 and 7; 2, 4, 5 and 7; 2, 4 and 8; 2, 4, 5 and 8; 2 and 9; 2 and 10; 2, 9 and 10; 3 and 4; 3, 4 and 5; 3, 4 and 6; 3, 4, 5 and 6; 3, 4 and 7; 3, 4, 5 and 7; 3, 4 and 8; 3, 4, 5 and 9; 3 and 9; 3 and 10; 3, 9 and 10; 4 and 5; 4 and 6; 4, 5 and 6; 4 and 7; 4, 5 and 7; 4 and 8; 4, 5 and 8; 4 and 9; 4 and 10; 4, 9 and 10; 9 and 10; 4 and 12; 10 and 12; and 11 and 12, any of which may be in further combination with element 11. The composition of C may be used in combination with any of the elements applicable to A.

To facilitate a better understanding of the embodiments described herein, the following examples of various representative embodiments are given. In no way should the following examples be read to limit, or to define, the scope of the invention.

EXAMPLES

Figure 4:
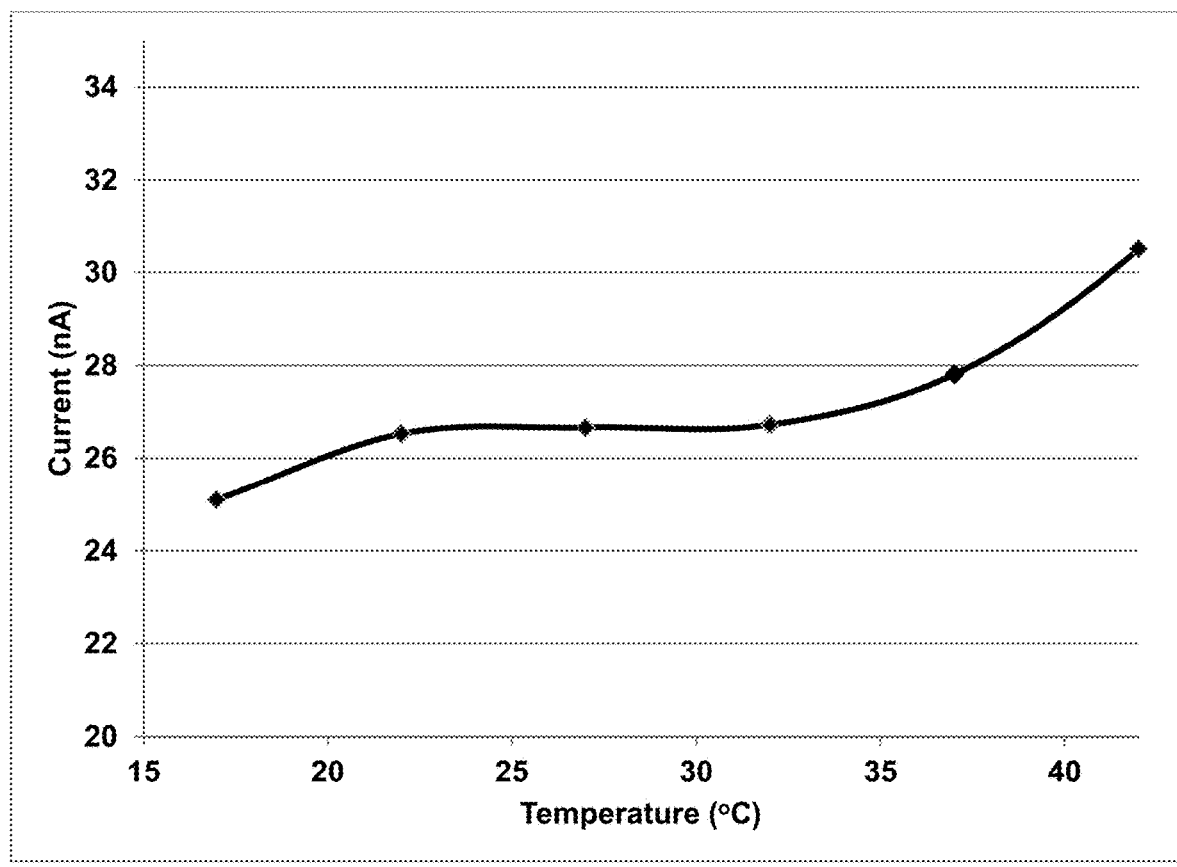
FIG. 4 shows an illustrative plot of sensor response over a temperature range of 17° C.-42° C. at a fixed glucose concentration, wherein the sensing region is overcoated with a polymeric membrane composition described herein.
Figure 5:
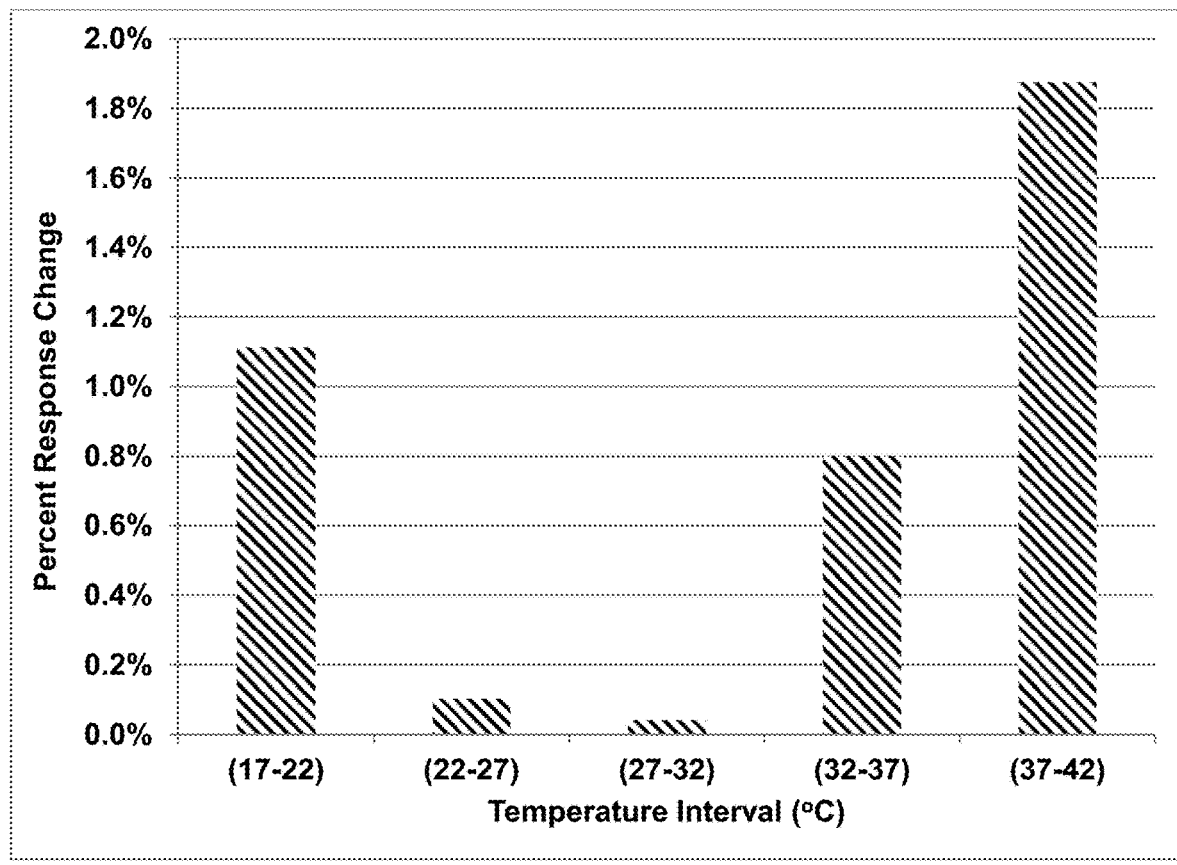
FIG. 5 shows an illustrative bar graph demonstrating the temperature variation over 5° C. increments for a sensor operating over a temperature range of 17° C.-42° C. at a fixed glucose concentration, wherein the sensing region is overcoated with a polymeric membrane composition described herein.

Example 1: Temperature Variability. A polyvinylpyridine copolymer with styrene having an amine-free polyether arm with a structure corresponding to Formula 12 (w=1, x=14, y=12, z=18) was coated on to a glucose responsive sensor. The coated sensor was then exposed to a glucose solution of fixed concentration, and the sensor response was measured over a range of temperatures. FIG. 4 shows a plot of sensor response data over a temperature range of 17° C.-42° C. As shown in FIG. 4, the sensor response showed minimal variation over a substantial portion of the temperature range, which encompasses normal physiological temperatures in humans. Even at temperatures when the beginnings of response variability began to be observed (i.e., greater than 37° C.), the response variability was still below 2% over the 5° C. measurement intervals, as shown in the bar graph of FIG. 5.

Figure 6:
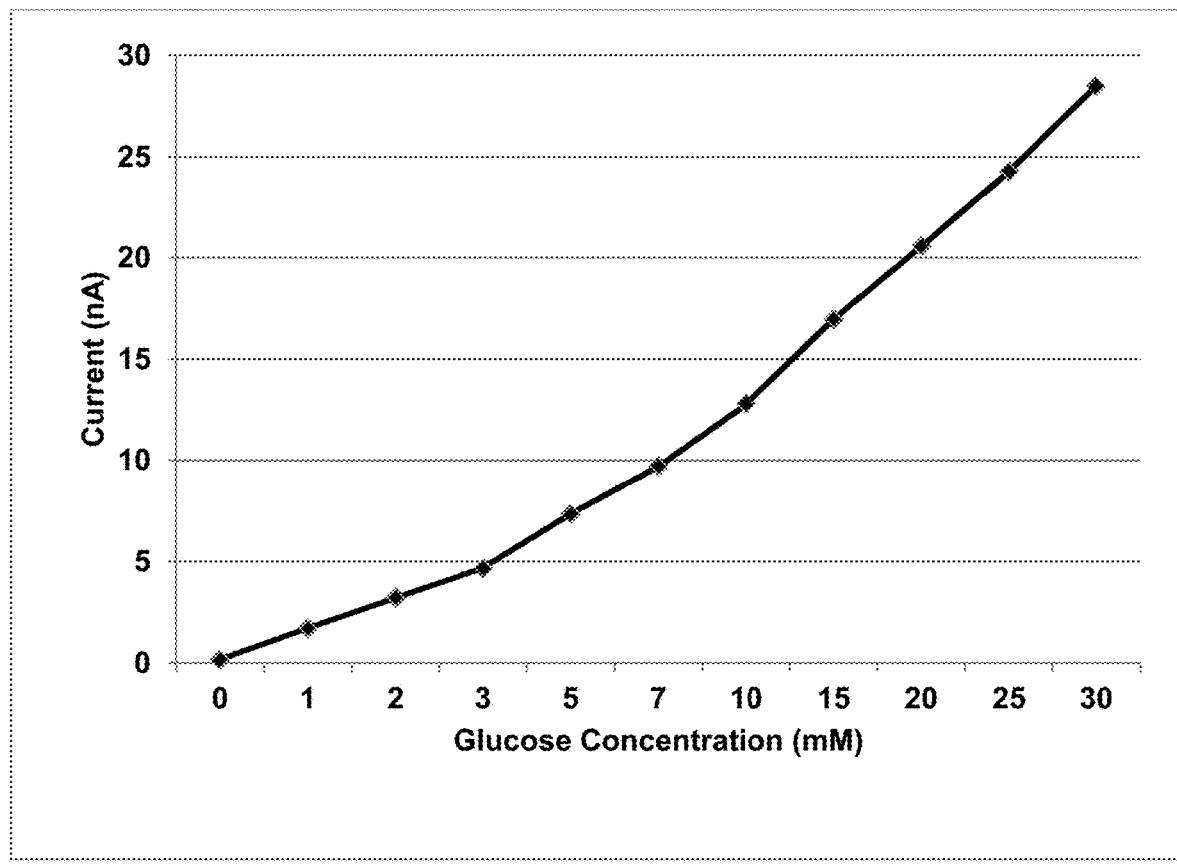
FIG. 6 shows an illustrative plot of sensor response versus glucose concentration at a constant temperature, wherein the sensing region is overcoated with a polymeric membrane composition described herein.

Example 2: Glucose Response. The coated sensor of Example 1 was tested at room temperature at variable glucose concentrations. As shown in FIG. 6, the sensor response as a function of glucose concentration was approximately linear at the fixed temperature.

Example 3: Biocompatibility Testing. Polyvinylpyridine copolymers with styrene having an amine-free polyether arms with a structure corresponding to Formula 12 (w=1) and defined by variables x, y and z, as specified in Table 1 below, were used for conducting several biocompatibility tests. Testing was conducted according to ISO 10993-1 protocols and may be described in brief below.

Cytotoxicity. Polymers having amine-free polyether arms were tested for cytotoxicity under standard conditions using the Minimal Essential Elution Media Test. Results are shown in Table 1. Cytotoxicity testing was conducted by applying an extract of the polymer (glucose-free Minimal Essential Media) to a test cell monolayer, incubating, and scoring based upon the degree of monolayer destruction and the amount of cell lysis. A score of '0' represents no observable monolayer destruction or cell lysis. Mild cytotoxicity is classified by a score of '2' or lower (<50% monolayer destruction with no extensive cell lysis). Scores of 2 or lower are considered acceptable criteria for certain purposes under current U.S. Pharmacopeia and National Formula requirements (<USP 87>).

TABLE 1

| Entry | x | y | z | (x + z):y | Cytotoxicity Score |
|---|---|---|---|---|---|
| 1 | 10 | 20 | 14 | 1.2 | 2 |
| 2 | 12 | 16 | 16 | 1.75 | 0 |
| 3 | 14 | 12 | 18 | 2.67 | 0 |

As shown in Table 1, increasing the ratio of polyethylene oxide to polypropylene oxide improved the cytotoxicity response.

Hemolysis. Hemolysis studies were conducted on the polymer of entry 3 using an extract method (phosphate buffered saline) as specified in ASTM F 756. There was no difference in hemolysis between the extract and a negative control, meaning that the polymer of entry 3 was non-hemolytic with a hemolysis index of 2 or below.

Mutagenicity. Mutagenicity studies were conducted on the polymer of entry 3 using the Ames test. Extracts of the polymer did not meet the requirements for mutagenicity under this test.

Single Dose Systemic Irritation Studies. An extract of the polymer of entry 3 was injected either intravenously or intraperitoneally. No signs of toxicity compared to the control were seen over the observation period.

Skin Irritation Studies. Skin irritation studies of an extract of the polymer of entry 3 produced a sensitization response score of 0, meaning no visible erythema or edema.

Intracutaneous Irritation Studies. Intracutaneous irritation studies of an extract of the polymer of entry 3 produced no abnormal clinical signs compared to the vehicle control over a 72-hour observation period. Calculated erythema and edema scores as compared to the control were less than 1 (no to barely perceptible erythema or edema).

Implantation Studies. The polymer of entry 3 produced an irritant score of 0.2 when implanted, thereby classifying it as a non-irritant.

Unless otherwise indicated, all numbers expressing quantities and the like in the present specification and associated claims are to be understood as being modified in all instances by the term "about." Accordingly, unless indicated to the contrary, the numerical parameters set forth in the following specification and attached claims are approximations that may vary depending upon the desired properties sought to be obtained by the embodiments of the present invention. At the very least, and not as an attempt to limit the application of the doctrine of equivalents to the scope of the claim, each numerical parameter should at least be construed in light of the number of reported significant digits and by applying ordinary rounding techniques.

One or more illustrative embodiments incorporating various features are presented herein. Not all features of a physical implementation are described or shown in this application for the sake of clarity. It is understood that in the development of a physical embodiment incorporating the embodiments of the present invention, numerous implementation-specific decisions must be made to achieve the developer's goals, such as compliance with system-related, business-related, government-related and other constraints, which vary by implementation and from time to time. While a developer's efforts might be time-consuming, such efforts would be, nevertheless, a routine undertaking for those of ordinary skill in the art and having benefit of this disclosure.

While various systems, tools and methods are described herein in terms of "comprising" various components or steps, the systems, tools and methods can also "consist essentially of" or "consist of" the various components and steps.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Therefore, the disclosed systems, tools and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems, tools and methods illustratively disclosed herein may suitably be practiced in the absence of any element that is not specifically disclosed herein and/or any optional element disclosed herein. While systems, tools and methods are described in terms of "comprising," "containing," or "including" various components or steps, the systems, tools and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces. If there is any conflict in the usages of a word or term in this specification and one or more patent or other documents that may be incorporated herein by reference, the definitions that are consistent with this specification should be adopted.

What is claimed is the following:

1. A polymeric membrane composition comprising:
   a polymer backbone comprising one or more side chains that comprise a heterocycle; and
   an amine-free polyether arm appended, via an alkyl spacer or a hydroxy-functionalized alkyl spacer, to the heterocycle of at least a portion of the one or more side chains;
   wherein the amine-free polyether arm comprises at least one polyethylene oxide block and at least one polypropylene oxide block, the amine-free polyether arm being bound to a heterocyclic or heteroaromatic nitrogen atom in a side chain of the polymer backbone.

2. The polymeric membrane composition of claim 1, wherein the polymer backbone comprises a polyvinylpyridine or a polyvinylimidazole.

3. The polymeric membrane composition of claim 2, wherein the polymer backbone comprises a copolymer of vinylpyridine and styrene.

4. The polymeric membrane composition of claim 1, wherein the amine-free polyether arm has a structure of

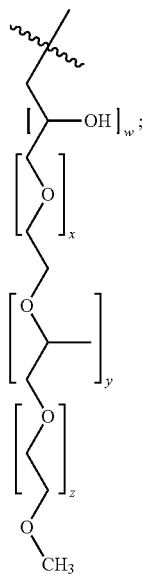

wherein w is 0 or 1, x ranges between about 4 and about 24, y ranges between about 8 and about 60, and z ranges between about 6 and about 36.

5. The polymeric membrane composition of claim 4, wherein x ranges between about 8 and about 16, y ranges between about 10 and about 32, and z ranges between about 10 and about 20.

6. The polymeric membrane composition of claim 4, wherein x≤z.

7. The polymeric membrane composition of claim 4, wherein a ratio of (x+z):y is at least about 1.7:1.

8. The polymeric membrane composition of claim 4, wherein a ratio of (x+z):y ranges between about 1.7:1 and about 5:1.

9. The polymeric membrane composition of claim 1, further comprising:
a sulfonate-containing arm appended to at least a portion of the one or more side chains.

10. The polymeric membrane composition of claim 1, further comprising:
an amine-free polyethylene oxide arm appended, via an alkyl spacer or a hydroxy-functionalized alkyl spacer, to the heterocycle of at least a portion of the one or more side chains.

11. The polymeric membrane composition of claim 1, further comprising:
a crosslinker appended to at least a portion of the one or more side chains and adjoining a first polymer backbone to a second polymer backbone.

12. The polymeric membrane composition of claim 1, wherein the polymeric membrane composition meets or exceeds ISO 10993-1 standards.

13. An analyte sensor comprising:
a sensing region; and
a polymeric membrane composition overlaying the sensing region;
wherein the polymeric membrane composition comprises a polymer backbone comprising one or more side chains that comprise a heterocycle, and an amine-free polyether arm appended, via an alkyl spacer or a hydroxy-functionalized alkyl spacer, to the heterocycle of at least a portion of the one or more side chains; and
wherein the amine-free polyether arm comprises at least one polyethylene oxide block and at least one polypropylene oxide block, the amine-free polyether arm being bound to a heterocyclic or heteroaromatic nitrogen atom in a side chain of the polymer backbone.

14. The analyte sensor of claim 13, wherein the sensing region comprises an enzyme.

15. The analyte sensor of claim 13, wherein the polymer backbone comprises a polyvinylpyridine or a polyvinylimidazole.

16. The analyte sensor of claim 15, wherein the polymer backbone comprises a copolymer of vinylpyridine and styrene.

17. The analyte sensor of claim 13, wherein the amine-free polyether arm has a structure of

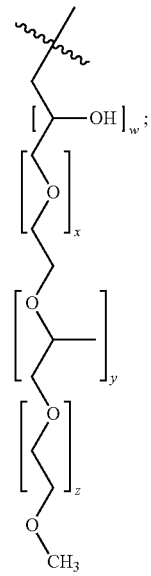

wherein w is 0 or 1, x ranges between about 4 and about 24, y ranges between about 8 and about 60, and z ranges between about 6 and about 36.

18. The analyte sensor of claim 17, wherein x ranges between about 8 and about 16, y ranges between about 10 and about 32, and z ranges between about 10 and about 20.

19. The analyte sensor of claim 17, wherein x≤z.

20. The analyte sensor of claim 17, wherein a ratio of (x+z):y is at least about 1.7:1.

21. The analyte sensor of claim 17, wherein a ratio of (x+z):y ranges between about 1.7:1 and about 5:1.

22. The analyte sensor of claim 13, further comprising:
a sulfonate-containing arm appended to at least a portion of the one or more side chains.

23. The analyte sensor of claim 13, further comprising:
an amine-free polyethylene oxide arm appended, via an alkyl spacer or a hydroxy-functionalized alkyl spacer, to the heterocycle of at least a portion of the one or more side chains.

24. The analyte sensor of claim 13, further comprising:
a crosslinker appended to at least a portion of the one or more side chains and adjoining a first polymer backbone to a second polymer backbone.

25. The polymeric membrane composition of claim 1, wherein the polymeric membrane composition is temperature-insensitive to at least glucose permeability over a temperature range of about 15° C. to about 45° C.

26. The polymeric membrane composition of claim 25, wherein the polymeric membrane composition meets or exceeds ISO 10993-1 standards.

* * * * *